United States Patent [19]

Bühmann et al.

[11] Patent Number: 4,983,755
[45] Date of Patent: Jan. 8, 1991

[54] SUBSTITUTED HYDRAZONES, PROCESS FOR THE PREPARATION AND THEIR USE AS PESTICIDE

[75] Inventors: Ulrich Bühmann; Dieter Hübl; Ernst-Albrecht Pieroh, all of Berlin, Fed. Rep. of Germany

[73] Assignee: Schering Aktiengesellschaft, Fed. Rep. of Germany

[21] Appl. No.: 74,973

[22] Filed: Jul. 17, 1987

[30] Foreign Application Priority Data

Jul. 17, 1986 [DE] Fed. Rep. of Germany ....... 3624349

[51] Int. Cl.$^5$ .................. C07C 271/12; C07C 269/06
[52] U.S. Cl. ........................................ 560/24; 560/30
[58] Field of Search ..................... 560/24, 30; 514/482

[56] References Cited

U.S. PATENT DOCUMENTS

| | | |
|---|---|---|
| 3,708,591 | 1/1973 | Bayer et al. |
| 3,867,425 | 2/1975 | Dusza et al. |
| 4,432,994 | 2/1984 | Giles et al. ........................... 514/482 |
| 4,570,002 | 2/1986 | Budai et al. ........................... 548/495 |

FOREIGN PATENT DOCUMENTS 0026040 4/1981 European Pat. Off.
2027705 2/1980 United Kingdom.

OTHER PUBLICATIONS

Hadzi et al., "Chem. Abst.", vol. 66, p. 8412, Item 89821b (1967); Collective Formula Index 1966-1975, $C_{13}H_{18}N_2O$, Acetic Acid, (alpha-tert-butylbenzylidene)-hydrazide.

*Primary Examiner*—Glennon H. Hollrah
*Assistant Examiner*—Jessica H. Nguyen
*Attorney, Agent, or Firm*—Ostrolenk, Faber, Gerb & Soffen

[57] ABSTRACT

A method of combatting plant nematodes which comprises applying to the soil or the plant, an effective amount of a compound of general formula I

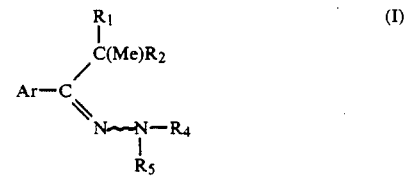

wherein
Ar, X, $R_1$, $R_2$, $R_4$ and $R_5$ have the meanings given in the description, is described. Some of the compounds also form part of the invention.

4 Claims, No Drawings

SUBSTITUTED HYDRAZONES, PROCESS FOR THE PREPARATION AND THEIR USE AS PESTICIDE

This invention relates to new substituted hydrazones and their use as pesticides, especially against nematodes.

Substituted hydrazones possessing insecticidal activity, have already been described, for example in EP No. 26 040 and U.S. Pat. No. 3,708,591. Whilst certain insecticides, e.g. aldicarb, also possess some nematicidal activity, most insecticides have little or no such activity. We have now found that certain substituted hydrazones possess very good nematicidal activity.

Thus the invention provides a method of combatting plant nematodes, which comprises applying to the soil or the plant, an effective amount of a compound of general formula I

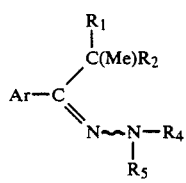

wherein

Ar is phenyl, optionally substituted by one or more groups selected from halogen, fluorinated methoxy, fluorinated ethoxy or trifluoromethyl, or is chlorothienyl;

$R_1$ is hydrogen, $C_{1-3}$-alkyl, optionally substituted by halogen, or is $C_{1-3}$-alkoxy;

$R_2$ is hydrogen or methyl;

$R_4$ is hydrogen, methyl, ethyl or $COR_6$; and $R_5$ is hydrogen,

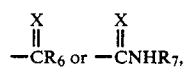

wherein

X is oxygen or sulphur;

$R_6$ is methyl, ethyl, phenyl, methoxy, ethoxy or propoxy, each of which is optionally substituted by halogen, or is hydrogen; and $R_7$ is hydrogen or methyl.

Some of the compounds are novel. Accordingly the invention also provides substituted hydrazones of general formula II

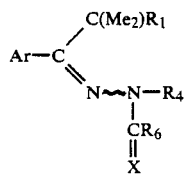

wherein

Ar is phenyl, optionally substituted by one or more groups selected from halogen, fluorinated methoxy, fluorinated ethoxy or trifluoromethyl, or is chlorothienyl;

$R_1$ is $C_{1-3}$-alkyl or $C_{1-3}$-alkoxy;

$R_4$ is hydrogen, methyl, ethyl or

$R_6$ is methyl, ethyl, methoxy or ethoxy, each of which is optionally substituted by one or more fluorine atoms, or is hydrogen; and X is oxygen or sulphur.

X is preferably oxygen.

The term "halogen" includes fluorine, chlorine, bromine and iodine. Where a group is substituted by halogen, unless otherwise specified, this can be by one or more of such atoms. Halothienyl is preferably 5-chlorothien-2-yl. Fluorinated methoxy and fluoroethoxy groups are generally di- or tri-substituted and are preferably difluoromethoxy and 2,2,2-trifluoroethoxy.

Particularly preferred compounds are those in which

Ar is phenyl, optionally substituted by one or two halogens;

$R_1$ is methyl or ethyl;

$R_4$ is hydrogen or methyl;

$R_6$ is hydrogen, methoxy or ethoxy; and

X is oxygen.

The compounds of the invention can exist in either geometric isomers, i.e. the syn or anti forms, or as a mixture of both isomers. In the general formula I, this is indicated by the wavy line between the two nitrogen atoms (N N).

The compounds of general formula II can be produced by known methods, in which a compound of general formula III

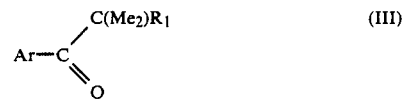

in which Ar and $R_1$, have the meanings given above, is reacted with a hydrazine derivative of general formula IV

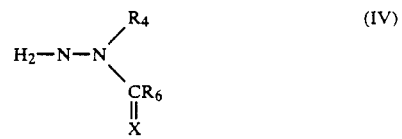

in which $R_4$ and $R_6$ have the meanings given above.

The reaction is suitably carried out in solvents which are inert to the hydrazine derivative, for example alcohols such as methanol, ethanol, isopropanol and propanol or aromatoc hydrocarbons, such as benzene, toluene and xylene or ethers, such as tetrahydrofuran, diethyl ether and dioxan, under anhydrous conditions and with the addition of acid catalysts, such as for example sulphuric acid, p-toluenesulphonic acid or hydrogen chloride gas.

The reaction is suitably carried out at atmospheric pressure and at a temperature in the range of 0° to 200° C., advantageously at a temperature between 40° and 140° C.

In some cases the reaction is advantageously carried out without a solvent in the molten state.

An alternative method is by reacting a compound of general formula V

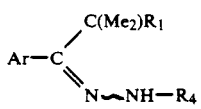

in which $R_1$ and $R_4$, have the meanings given above, with a compound of general formula VI

in which X and $R_6$ have the meanings given above and Z is a leaving group, such as chlorine or $C_{1-4}$-alkoxy.

The compounds of formula III and V are either known or can be prepared by known processes (e.g. J. Am. Chem. Soc. 72, (1950), 4169–4170).

The other starting materials are for the most part commercial products or can easily be prepared by methods well known to the man skilled in the art.

Because of the nematicidal activity coupled with good plant compatibility, the compounds according to the invention can be successfully applied in plant protection as pesticides in agriculture, in vine and fruit growing, in horticulture and in forestry.

Plant Parasitic nematodes which can be controlled according to the invention include for example root-knot nematodes, such as Meloidogyne incognita, Meloidogyne hapla and Meloidogyne javanica, cyst forming nematodes, such as Globodera rostochiensis, Heterodera schacktii, Heterodera avanae, Heterodera glycines and Heterodera trifolii, and stem and leaf eelworms, such as Ditylenchus dipsaci, Ditylenchus destructor, Aphelenchoides ritzemabosi, Pratylenchus neglectus, Tylenchorhynchus dudius, Tylenchorhynchus claytoni, Rotylenchus robustus, Heliocotylenchus multicinctus, Radopholus similis, Belonolaimus longicaudatus, Longidorus elongatus and Trichodorus primitivus.

Many of the compounds of formula I and II also have insecticidal activity for example against Lepidoptera, such as *Plutella xylostella, Spodoptera littoralis, Heliothis armigera* and *Pieris brassicae;* Diptera, such as *Musca domestica, Ceratitis capitata, Erioischia brassicae. Lucilia sericata* and *Aedes aegypti;* Homoptera, including aphids such as *Megoura viciae* and *Nilaparvata lugens;* Coleoptera, such as *Phaedon cochleariae, Anthonomus grandis* and *Epilachna varivestis* and corn rootworms (*Diabrotica* spp., e.g. *Diabrotica undecimpunctata*); Orthoptera, such as cockroaches e.g. *Blattella germanica;* Hymenoptera, such as ants e.g. *Monomorium pharaonis;* mange mites, e.g. Sarcoptes spp.; as well as spider mites such as *Tetranychus urticae* and *Panonychus ulmi.*

The compounds of the invention can be used in the commercial formulations and/or as the preparations for use prepared from these formulations. The content of active ingredient in the preparations for use from the the commercial formulations can vary over a wide range. The rate of use per hectare is for example about 0.03 kg to 10 kg, preferably about 0.3 kg to about 6 kg.

The active ingredient can be applied in the usual formulations such as solutions, emulsions, wettable powders, suspensions, powders, dusts, foams, pastes, soluble powders, granules, aerosols, suspension concentrates, seed dressings, natural and synthetic substances impregnated with the active ingredients, microcapsules in polymers and in seed coatings for seeds, as well as formulations with burning substances such as smoke cartridges, smoke capsules and smoke spirals amongst others as well as ULV-cold and hot fogging formulations.

These formulations can be prepared in known manner for example by mixing the active ingredient with diluents such as liquid solvents and liquefied gases and/or solid carriers, optionally using surface active agents such as emulsifiers and/or dispersing agents and/or foaming agents. When using water as the diluent, organic solvents can also be used for example as auxiliary solvents. Examples of liquid solvents include aromatic hydrocarbons, such as xylene, toluene or alkynaphthalene, chlorinated aromatic or chlorinated aliphatic hydrocarbons, such as chlorobenzene, chloroethylene or methylene dichloride, aliphatic hydrocarbons, such as cychlohexane or paraffins, for example mineral oil fractions, alcohols, such as butanol and glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By the term liquefied gaseous diluents or carriers are meant those substances which are gaseous at normal temperature and pressure, for example aerosol blowing agents, such as halohydrocarbons as well as butane, propane, nitrogen and carbon dioxide. Examples of solid carriers are natural earth powders, such as kaolin, alumina, talc, chalk, quartz, attapulgite, montmorillonite or diatomaceous earths and synthetic powders, such as finely divided silica, aluminium oxide and silicates as well as solid carriers for granules, crushed and fractionated natural rocks, such as calcite, marble, pumice, sepiolith and dolomite, as well as synthetic granules from inorganic and organic powders as well as granules from organic materials such as sawdust, coconut shells, maize cobs amd tobacco stalks. Examples of emulsifying and/or foaming agents include non-ionic and anionic emulsifiers such as polyoxyethylene-fatty acid esters, polyoxyethylene-fatty alcohol ethers, for example alkylaryl-polyglycol-ethers, alkylsulphonates and arylsulphonates as well as protein hydrolysates. Dispersing agents include for example lignin, sulphite waste liquors and methylcellulose. There can also be used in the formulations sticking agents such as carboxymethylcellulose, natural and synthetic powdery, granulated or latex-forming polymers, as well as gum arabic, polyvinyl alcohol and polyvinyl acetate. There can also be used dyestuffs, such as inorganic pigments, for example iron oxide, titanium oxide, ferrocyan blue and organic dyestuffs such as alizarin- and azo-metal phthalocyanine dyestuffs and trace elements such as salts of iron, manganese, boron, copper, cobalt, molybdenum and zinc.

The formulations contain in general between 0.1 and 95 weight percent of the active ingredient, preferably between 0.5 and 90 percent.

Powders and dusts can be prepared by mixing or milling the active ingredient with a solid carrier.

Examples of formulations are:

I. 10 parts by weight of compound No.1 are intimately mixed with 90 parts by weight of finely divided kaolin. In this way a dusting powder is obtained that contains 10% by weight of active ingredient.

II. 30 parts by weight of compound No.5 were intimately mixed with a mixture of 92 parts by weight of finely divided silica gel and 8 parts by weight of paraffin oil that had been sprayed on the surface of the silica gel. In this way there is obtained a dressing containing the active ingredient with good adhesiveness.

III. 10 parts by weight of compound No.6 were dissolved in a mixture of 90 parts by weight of xylene, 6 parts by weight of an addition product comprising 8 to 10 moles of ethylene oxide to 1 mole of oleic acid N-monoethanolamide, 2 parts by weight of calcium of dodecylbenzenesulphonate and 2 parts by weight of the addition product of 40 moles of ethylene oxide and 1 mole of castor oil.

IV. 20 parts by weight of compound No.11 were dissolved in a mixture of 60 parts by weight of cyclohexanone, 30 parts by weight of isobutanol, 5 parts by weight of the reaction product of 7 moles of ethylene oxide to 1 mole of isooctylphenol and 5 parts by weight of the reaction product of 40 moles of ethyleneoxide and 1 mole of castor oil.

V. 80 parts by weight of compound No.18 were mixed well with 3 parts by weight of sodium salt ligninsulphonate from sulphite waste liquors and 7 parts by weight of powdery silica gel and then milled in a hammer mill.

The following examples illustrate the preparation of compounds of the invention.

EXAMPLE 1

Ethyl 3-[1-(4-chlorophenyl)-2,2-dimethylpropylidene]carbazate

A solution of 4.92 g (0.025 mol) 4-chlorphenyl tert.-butyl ketone and 8.05 g (0.075 mol) ethyl carbazate in 125 ml absolute ethanol was treated with ca. 0.3 g concentrated sulphuric acid and heated at reflux for 3 hours. The solution was then concentrated in vacuo and the residue added to water. It was then extracted with ethyl acetate, the organic phase dried with magnesium sulphate, concentrated and the residue recrystallised from diisopropyl ether.

Yield: 5.5 g = 77.1% of theory.
m.p.: 125°–126° C.

Elementary analysis: Calculated: 59.46% C 6.77% H 12.54% Cl 9.91% N. Found: 59.28% C 6.82% H 13.00% Cl 9.99% N.

EXAMPLE 2

Methyl 3-[1-(4-chlorophenyl)-2,2-dimethylpropylidene-2-methylcarbazate 3 g (0.013 mol) of 4-chlorophenyl tert.-butyl ketone N-methylhydrazone was dissolved in 30 ml methylene chloride and treated with 1.5 g triethylamine (0.014 mol). Then, at 0° C., 1.33 g (0.014 mol) methyl chloroformate was added dropwise and the mixture stirred for one hour. The reaction mixture was then treated with water and methylene chloride and the organic phase dried and concentrated. After thin layer chromatography, there was obtained methyl 3-[1-(4-chlorophenyl)-2,2-dimethylpropylidene]-2-methylcarbazate, m.p. 58°–60° C.

Yield: 2.47 g = 67.1% of theory.

Elementary analysis: Calculated: 59.46% C 6.77% H 9.91% N 12.54% Cl. Found: 59.46% C 6.77% H 9.80% N 12.97% Cl.

Preparation of the starting material, 4-chlorophenyl tert.-butyl ketone N-methylhydrazone 29.5 g ofg 4-chlorophenyl tert.-butyl ketone (0.15 mol) in 750 ml ethanol was heated under reflux with an excess (118 ml) of methl hydrazine and 3 ml of concentrated sulphuric acid for 4.5 hours. It was concentrated almost to dryness and the added to water. After extraction with methylene chloride and then drying and concentrating the extract in vacuo, there was obtained an oil which eventually crystallised. The resulting crude product used immediately.

Yield: 33.7 g = 100% of theory (based on the ketone).

EXAMPLE 3

The following compounds were prepared in an analogous manner.

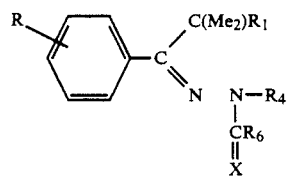

| No | R | $R_1$ | X | $R_4$ | $R_6$ | m.p. (°C.) or $n_D^{20}$ |
|----|---|-------|---|-------|-------|--------------------------|
| 3  | 4-Cl | $C_2H_5$ | O | H | $OC_2H_5$ | 97–98 |
| 4  | 4-F | $CH_3$ | O | H | $OC_2H_5$ | 125–127 |
| 5  | 4-Br | $CH_3$ | O | H | $OC_2H_5$ | 137–138 |
| 6  | 3-Br | $CH_3$ | O | H | $OC_2H_5$ | 112–113 |
| 7  | — | $CH_3$ | O | H | $OC_2H_5$ | 106–108 |
| 8  | 4-Cl | $CH(CH_3)_2$ | O | H | $OC_2H_5$ | 88–90 |
| 9  | 3,4-diCl | $CH_3$ | O | H | $OC_2H_5$ | 149–151 |
| 10 | 4-Cl | $CH_3$ | O | H | $OCH_3$ | 167–169 |
| 11 | 4-$CF_3$ | $CH_3$ | O | H | $OCH_3$ | 123–125 |
| 12 | 4-$CF_3$ | $CH_3$ | O | H | $OC_2H_5$ | 133–135 |
| 13 | 4-Cl | $CH_3$ | O | H | $OC_3H_7$ | 128–129 |
| 14 | 4-Cl | $CH_3$ | O | H | $OCH(CH_3)_2$ | 173–174 |
| 15 | 4-$CHF_2$ | $CH_3$ | O | H | $OC_2H_5$ | 92–93 |
| 16 | 4-$CF_3CH_2O$ | $CH_3$ | O | H | $OC_2H_5$ | 100–101 |
| 17 | 4-$CF_3CH_2O$ | $CH_3$ | O | H | $OCH_3$ | 108–110 |
| 18 | 4-Cl | $C_3H_7$ | O | H | $OC_2H_5$ | 80.5–81 |
| 19 | 4-Cl | $C_2H_5$ | O | H | $OCH_3$ | 109–110 |
| 20 | 4-Cl | $OC_2H_5$ | O | H | $OC_2H_5$ | 91–93 |
| 21 | 4-Cl | $OC_3H_7$ | O | H | $OC_2H_5$ | 92–94 |
| 22 | 4-Cl | $OC_3H_7$ | O | H | $OCH_3$ | 81–83 |

-continued

| No | Ar | R | | R5 | R6 | m.p. |
|---|---|---|---|---|---|---|
| 23 | 4-Cl | CH₃ | O | H | CH₃ | 174-174 |
| 24 | 4-Cl | CH₃ | O | H | C₂H₅ | 148 |
| 25 | 4-Cl | CH₃ | O | H | H | 136-138 |
| 26 | 4-Cl | CH₃ | O | H | CF₃ | 124-126 |
| 27 | 4-Cl | C₃H₇ | O | H | OCH₃ | 123-125 |
| 28 | — | CH₃ | O | H | OCH₃ | 82-83 |
| 29 | 4-F | CH₃ | O | H | OCH₃ | 158-9 |
| 30 | 4-Br | CH₃ | O | H | OCH₃ | 163-4 |
| 31 | — | CH₃ | O | H | H | 74-76 |
| 32 | 4-F | CH₃ | O | H | H | 110-111 |
| 33 | 4-Br | CH₃ | O | H | H | 144-147 |
| 34 | 4-Cl | CH₃ | O | COOCH₃ | OC₂H₅ | >200 |
| 35 | 4-Cl | CH₃ | O | COCH₃ | OC₂H₅ | >200 |
| 36 | 4-Cl | CH₃ | O | CH₃ | OC₂H₅ | >200 |
| 37 | 4-F | CH₃ | O | C₂H₅ | OC₂H₅ | 1.4900 |
| 38 | 3-F | CH₃ | O | H | OCH₃ | 110 |
| 39 | 3-F | CH₃ | O | H | OC₂H₅ | 90 |
| 40 | 3-CF₃ | CH₃ | O | H | OCH₃ | 111 |
| 41 | 3-CF₃ | CH₃ | O | H | OC₂H₅ | 98 |
| 42 | — | CH₃ | O | H | CH₃ | 72-73 |
| 43 | — | CH₃ | O | H | CF₃ | 68-70 |
| 44 | — | CH₃ | O | CH₃ | OCH₃ | 1.5015 |
| 45 | 4-F | CH₃ | O | H | CH₃ | 131-133 |
| 46 | 4-F | CH₃ | O | H | CF₃ | 111-112 |
| 47 | 4-F | CH₃ | O | CH₃ | H | 46-48 |
| 48 | 4-F | CH₃ | O | CH₃ | OCH₃ | 1.4956 |
| 49 | 4-Br | CH₃ | O | H | CH₃ | 177-180 |
| 50 | 4-Br | CH₃ | O | H | CF₃ | 125-127 |
| 51 | 4-Br | CH₃ | O | CH₃ | H | 94-96 |
| 52 | 4-Br | CH₃ | O | CH₃ | OCH₃ | 62-63 |
| 53 | 4-Cl | CH₃ | O | CH₃ | H | 84-85 |
| 54 | 4-Cl | CH₃ | O | CH₃ | CF₃ | 1.4950 |
| 55 | — | CH₃ | O | CH₃ | H | 1.5290 |
| 56 | 4-Cl | CH₃ | O | C₂H₅ | H | 73-75 |
| 57 | 4-Cl | CH₃ | O | C₂H₅ | OCH₃ | 62-64 |
| 58 | 4-Cl | CH₃ | S | H | OCH₃ | 112-115 |
| 59 | 4-Cl | CH₃ | S | H | OC₂H₅ | 92-94 |
| 60 | 4-F | CH₃ | S | H | OCH₃ | 80-82 |
| 61 | 4-F | CH₃ | S | H | OC₂H₅ | 67-69 |
| 62 | 3-CHF₂O | CH₃ | O | H | OCH₃ | 55 |
| 63 | 3-CHF₂O | CH₃ | O | H | OC₂H₅ | 25 |
| 64 | 3-Cl | CH₃ | O | H | OCH₃ | 115 |
| 65 | 2-F | CH₃ | O | H | OCH₃ | 106 |
| 66 | 3-Cl | CH₃ | O | H | OC₂H₅ | 85 |
| 67 | 4-Cl | CH₃ | O | CHO | OCH₃ | 73-75 |
| 68 | — | OCH₃ | O | H | OCH₃ | 76-78 |
| 69 | — | OCH₃ | O | H | OC₂H₅ | 58-59 |
| 70 | — | OCH₃ | O | H | H | 49-51 |
| 71 | 4-Cl | OCH₃ | O | H | OCH₃ | 119-120 |
| 72 | 4-Cl | OCH₃ | O | H | OC₂H₅ | 119-120 |
| 73 | 2-F | CH₃ | O | H | OC₂H₅ | 78 |
| 74 | 2,4-diF | CH₃ | O | H | OCH₃ | 169 |
| 75 | 2,4-diF | CH₃ | O | H | OC₂H₅ | 127 |
| 76 | 4-Cl | OC₂H₅ | O | H | OC₂H₅ | 91-93 |
| 77 | 4-Cl | OC₃H₇ | O | H | OCH₃ | 81-83 |
| 78 | 4-Cl | OC₃H₇ | O | H | OC₂H₅ | 91-93 |

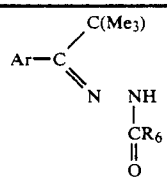

| No | Ar | R₆ | m.p. (°C.) |
|---|---|---|---|
| 79 | 5-Cl-thien-2-yl | OCH₃ | 121 |
| 80 | 5-Cl-thien-2-yl | OC₂H₅ | 68-70 |
| 81 | 2,5-diCl-thien-3-yl | OCH₃ | 133 |
| 82 | 2,5-diCl-thien-3-yl | OC₂H₅ | 115 |
| 83 | 5-Cl-thien-2-yl | H | 76 |

EXAMPLE 4

The following compounds were also prepared and shown to have nematicidal activity in accordance with the Test Example.

| | | | | | |
|---|---|---|---|---|---|
| A | 4-Cl-Ph | CH$_3$ | CH$_3$ | CSNHCH$_3$ | 160–162 |
| B | 4-Cl-Ph | CH$_3$ | CH$_3$ | H | 110–112 |
| C | 4-Cl-Ph | CH$_3$ | CH$_3$ | CSNH$_2$ | 192–194 |
| D | 4-Cl-Ph | CH$_3$ | CH$_3$ | COC$_6$H$_5$ | 1455 |
| E | 4-Cl-Ph | CH$_3$ | H | COOC$_2$H$_5$ | 88–90 |
| F | 4-F-Ph | CH$_3$ | H | COOC$_2$H$_5$ | 86–87 |
| G | 4-Br-Ph | CH$_3$ | H | COOC$_2$H$_5$ | 98–100 |
| H | Ph | CH$_3$ | H | COOC$_2$H$_5$ | >200 |
| I | 4-Cl-Ph | H | H | COOC$_2$H$_5$ | 104–106 |
| J | 4-Cl-Ph | CH$_3$ | CH$_2$Br | COOC$_2$H$_5$ | 95–96 |
| K | Ph | CH$_3$ | CH$_3$ | H | 44–45 |
| L | 4-F-Ph | CH$_3$ | CH$_3$ | H | 98–100 |
| M | 4-Cl-Ph | CH$_3$ | CH$_3$ | COCH$_2$Cl | 116–118 |
| N | Ph | CH$_3$ | CH$_3$ | COCH$_2$Cl | 79–80 |
| O | 4-Br-Ph | CH$_3$ | CH$_3$ | COCH$_2$Cl | 137–138 |
| P | 5-Cl-thien-2-yl | CH$_3$ | CH$_3$ | H | 74 |

TEST EXAMPLE

Control of root knot nematode, *Meloidogyne incognita* (Chitwood 1949).

10% of a powder preparation of the active ingredient prepared according to preparation No.I was mixed thoroughly with soil that had been strongly infested with the test nematode. After this the treated soil was put into a 0.5 liter fermenting tube, treated with cucumber seeds and cultivated at a soil temperature of 25° to 27° C. in a greenhouse. After a cultivation time of 25 to 28 days the cucumber roots were washed and inspected in a water bath for nematode attack (root knots) and the % level of activity of the active ingredients compared with a treated control was determined. When the nematode attack is fully controlled the level of activity is 100%

At a dose of 200 mg or less of active substance per liter of soil, a nematode attack by *Meloidogyne incognita* can be fully controlled (100%) by compounds 1–83 and A to P.

We claim:

1. Substituted hydrazone of the formula II

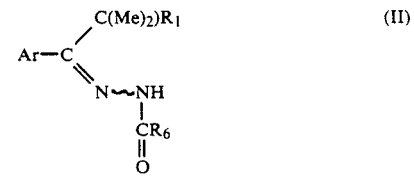

wherein

Ar is phenyl, substituted in the para position by one or more members of the group consisting of halogen, fluorinated methoxy, fluorinated ethoxy and trifluoromethyl:

R$_1$ is methyl or ethyl; and

R$_6$ is methoxy or ethoxy.

2. Compound according to claim 1 wherein Ar is halophenyl.

3. Compound according to claim 2 in which Ar is 4-chlorophenyl, R$_1$ is methyl and R$_6$ is methoxy.

4. Compound according to claim 1 wherein R$_1$ is methyl.

* * * * *